(12) United States Patent
Sengupta

(10) Patent No.: US 7,213,459 B2
(45) Date of Patent: May 8, 2007

(54) HIGH SPEED INSPECTION SYSTEM AND METHOD

(75) Inventor: Anandraj Sengupta, Bangalore (IN)

(73) Assignee: General Electric Company, Niskayuna, NY (US)

( * ) Notice: Subject to any disclaimer, the term of this patent is extended or adjusted under 35 U.S.C. 154(b) by 90 days.

(21) Appl. No.: 10/808,075

(22) Filed: Mar. 24, 2004

(65) Prior Publication Data

US 2005/0210984 A1    Sep. 29, 2005

(51) Int. Cl.
   *G01N 29/265* (2006.01)
(52) U.S. Cl. .................................................. 73/636
(58) Field of Classification Search ................. 73/635, 73/636, 639
See application file for complete search history.

(56) References Cited

U.S. PATENT DOCUMENTS

| | | | | |
|---|---|---|---|---|
| 3,415,110 A | * | 12/1968 | Cowan .......................... | 73/609 |
| 3,771,354 A | * | 11/1973 | Miller .......................... | 73/639 |
| 4,165,648 A | * | 8/1979 | Pagano .......................... | 73/625 |
| 4,291,577 A | * | 9/1981 | Baum et al. .................... | 73/597 |
| 4,519,251 A | * | 5/1985 | Dickson ........................ | 73/639 |
| 5,339,692 A | * | 8/1994 | Shoenhair et al. ............ | 73/636 |
| 5,341,683 A | * | 8/1994 | Searle .......................... | 73/597 |
| 5,419,196 A | * | 5/1995 | Havira et al. ................. | 73/636 |
| 5,522,265 A | | 6/1996 | Jaeggi et al. | |
| 6,055,862 A | * | 5/2000 | Martens ....................... | 73/632 |

FOREIGN PATENT DOCUMENTS

EP    0 722 085 A1    7/1996

OTHER PUBLICATIONS

R. Aharoni, et al "A Novel High-Speed Rail Inspection System", Retrieved on the Internet at URL http://www.ndt.net/article/ecndt02/156/156.htm , Oct. 2002, vol. 7, No. 10, 8 pages.

* cited by examiner

*Primary Examiner*—Hezron Williams
*Assistant Examiner*—Rose M. Miller
(74) *Attorney, Agent, or Firm*—Paul J. DiConza; William E. Powell, III

(57) ABSTRACT

An inspection system for inspecting a three-dimensional volume. The inspection system comprises at least one sensor coupled to a rolling object, the sensor being disposed on a non-contact outer region of the rolling object and at a pre-determined distance from a center of the rolling object. The sensor is configured to generate a signal representative of a condition of a region on the three dimensional volume.

20 Claims, 6 Drawing Sheets

HIGH SPEED INSPECTION SYSTEM AND METHOD

BACKGROUND

The invention relates generally to inspection systems, and more specifically to a system and method for inspecting objects at high speeds.

Inspection of railway tracks is one example where inspection systems are suitable for use. A typical inspection system used to inspect railway tracks includes sensors like ultrasound sensors or eddy current sensors that scan the tracks for known defect types and data storage and an analyzer to record and give out meaningful information from the scans. The sensors are generally placed in contact or close proximity of the track and are typically attached to a wheel (or inspection wheel) that rolls over the track as the train moves. In particular, the sensors are mounted on the center of the wheel which can restrict the speed of operation of the inspection device to the speed of the locomotive.

Typically, such inspection systems require high resolution data. In order to obtain high resolution, the scan speeds are required to be substantially low such as 30 miles per hour. Such requirements impose a limitation on the train speed because as mentioned above, the sensors are usually mounted on the wheels of the train. However, in order to perform real time inspection of the tracks, the inspection system is usually required to be implemented at higher speeds. A problem that arises is that, the obtained data resolution is significantly low as a result of higher speeds of operation. Data resolution is an important parameter for the accurate detection of flaws in railroad tracks.

Therefore, it is desirable to design an inspection system which can be operable at high speeds without effecting the data resolution.

BRIEF DESCRIPTION OF THE INVENTION

Briefly, according to one embodiment of the invention, an inspection system for inspecting a three-dimensional volume is provided. The system comprises at least one sensor coupled to the rolling object, wherein the at least one sensor is disposed on a non-contact outer region of the rolling object and at a pre-determined distance from a center of the rolling object. The sensor is configured to generate a signal representative of a condition of a region on the three dimensional volume. The system further comprises a data analyzer configured to analyze the signals to determine the condition of the three-dimensional volume at specific locations therein.

According to another embodiment of the invention, a method for inspecting a three-dimensional volume is provided. The method comprises translating a rolling object over a surface of the three-dimensional volume at a high speed, wherein the rolling object comprises at least one sensor coupled thereto, disposed on a non-contact outer region of the rolling object at a pre-determined distance from its center. The method further comprises sensing signals reflected from the three-dimensional volume as the rolling object translates over the three-dimensional volume.

In an alternate embodiment, an inspection system for inspecting a railway track is provided. The inspection system comprises at least one sensor coupled to a wheel of a locomotive, wherein the at least one sensor is disposed on a non-contact outer region of the wheel and at a pre-determined distance from a center of the wheel as it translates over the railway track at a high speed. The sensor is configured to generate a signal representative of a condition of a region on the railway track. The inspection system further comprises a data analyzer configured to analyze the signals to determine the condition of the railway track at specific locations therein.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
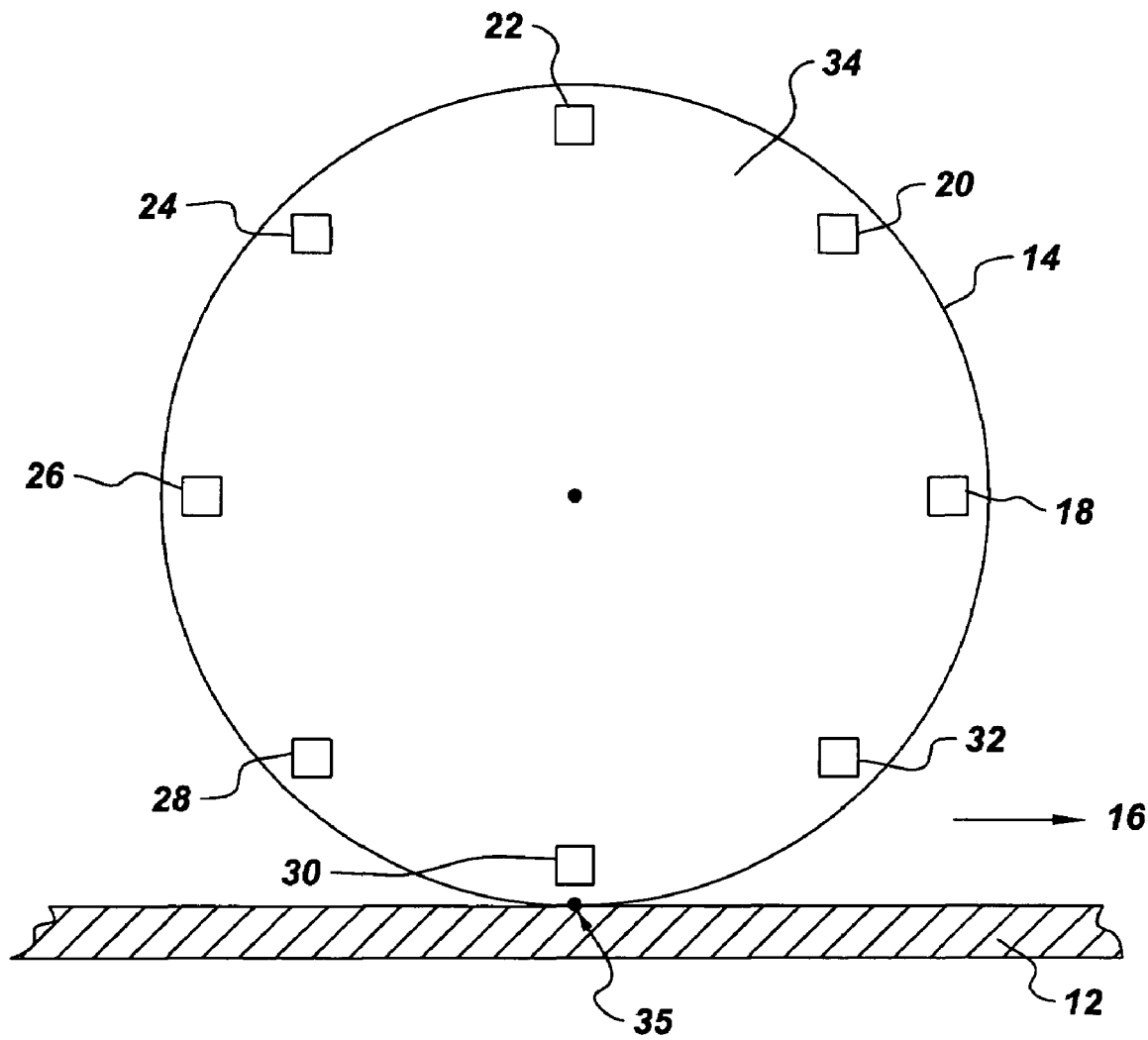
FIG. 1 is a front view of an embodiment of an inspection system implemented in the invention.

FIG. 1 is a front view of an embodiment of an inspection system 10 implemented in the invention. FIG. 1 illustrates a rolling object 14 translating over a three-dimensional volume 12 towards a direction noted by reference element 16. Each component of FIG. 1 is described in detail below.

As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to provide an output in response to given input signals.

Sensors 18, 20, 22, 24, 26, 28, 30 and 32 are coupled to the rolling object as shown. In one embodiment as illustrated in FIG. 1, the sensors are glued to the rolling object. In an alternate embodiment, the sensors are embedded in the rolling object. One of ordinary skill in the art will recognize that there are other approaches to attaching the sensors to the rolling object and the invention is not limited to the specific embodiments described herein. The sensors are disposed on a non-contact outer region 34 of the rolling object. In one embodiment, the sensors are ultrasonic sensors. Ultrasound transducers are typically piezoelectric ceramic crystals. Typically, the ultrasound sensor operates in two modes. In the first mode the crystals act as a ultrasound transmitter and in the latter mode as an ultrasound sensor. The sensors are configured to transmit ultrasound signals to the three-dimensional volume and receive the reflected signals. The reflected signals are converted to a corresponding electrical signal that representative of the three-dimensional volume inspected.

The rolling object translates over the three-dimensional volume at a translation velocity. In one embodiment, the translation velocity ranges from about 100 miles per hour (mph) to about 200 mph. In another embodiment, the three-dimensional volume is stationary. In an alternate embodiment, the three-dimensional volume is in motion.

Figure 2:
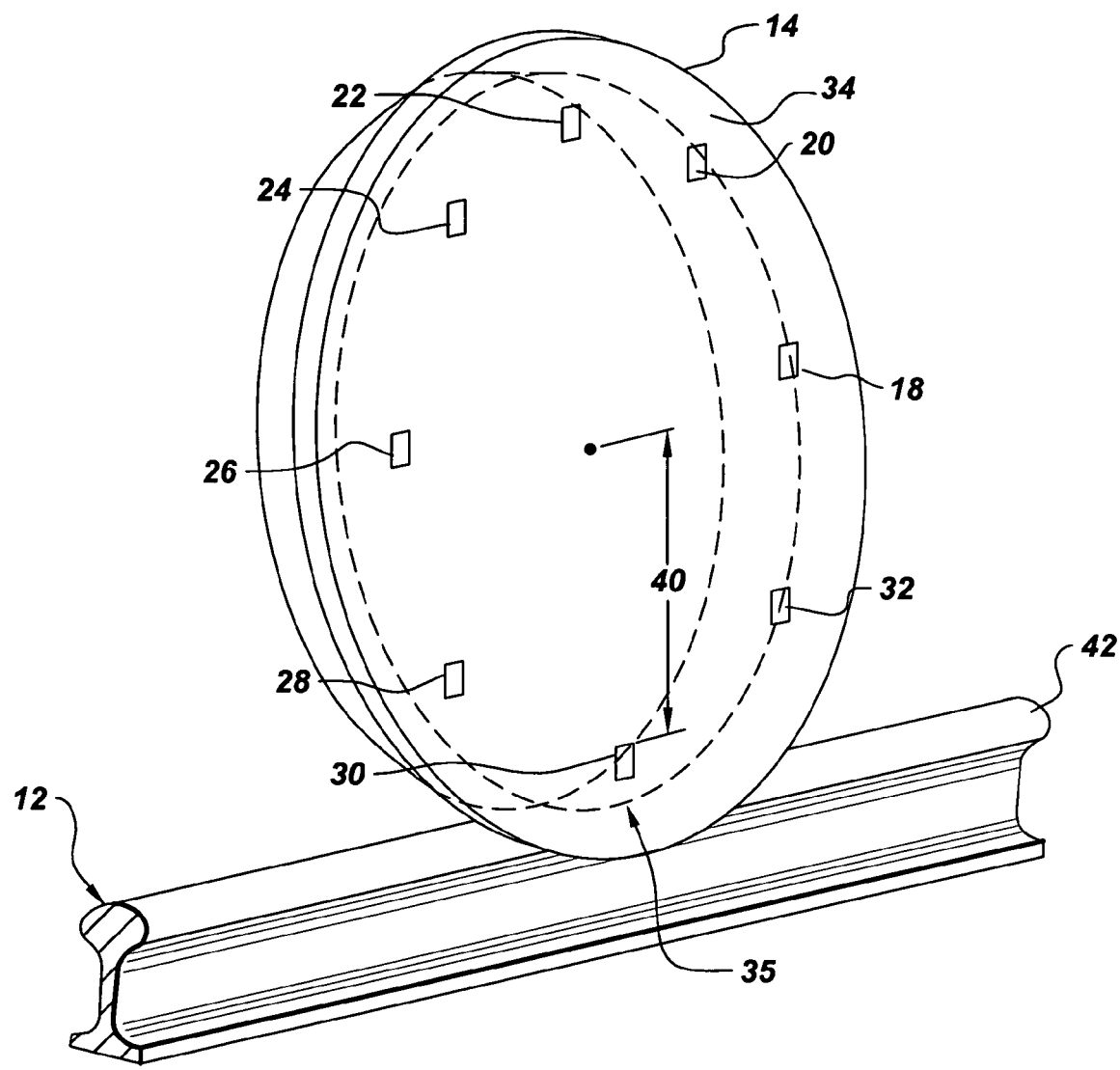
FIG. 2 is a three-dimensional view of the inspection system shown in FIG. 1.

The invention can be implemented in variety of applications such as a quality-monitoring system in a steel mill, however, the invention will be described with reference to an inspection system used to inspect a condition of a railway track. FIG. 2 illustrates a three-dimensional view of the rolling object 14 translating over the three-dimensional volume 12 which is the railway track. In one embodiment, the sensors are disposed at pre-determined distance 40 from a center 38 of the rolling object. In a more specific embodiment, the sensors are disposed at a periphery of the non-contact outer region of the rolling object.

When the rolling object is executing pure rolling motion, the lowest point of the rolling object 35 is at instantaneous rest. The points on the wheel around this lowest point have velocities that lie between zero and the translation velocity of the rolling object which for high speed applications can range from about 0 to about 200 mph. By disposing the sensors on the periphery of the rolling object, the relative velocity between sensor and three-dimensional volume is much lower than the translation velocity of the rolling object.

Referring to FIG. 2, the sensors are distributed close to the periphery of the rolling object. The sensors are activated sequentially such that the sensor closest to the point of rolling 35 is active at any instant of time. Point of rolling is referred to as the point at which the rolling object is in contact with a surface 42 of the three-dimensional volume 12.

The relative velocity experienced by an active sensor (sensor 30 in FIG. 2) is orders of magnitude lower than the translation velocity of the rolling object. In one example, the translation velocity of the rolling object is 90 m/s (200 mph) and the sensor relative speed is below 10 m/s (22 mph). The low sensor relative speed provides for ample data resolution because the sensor stays at one place for a longer time, irrespective of the train moving at much higher speeds.

Figure 3:
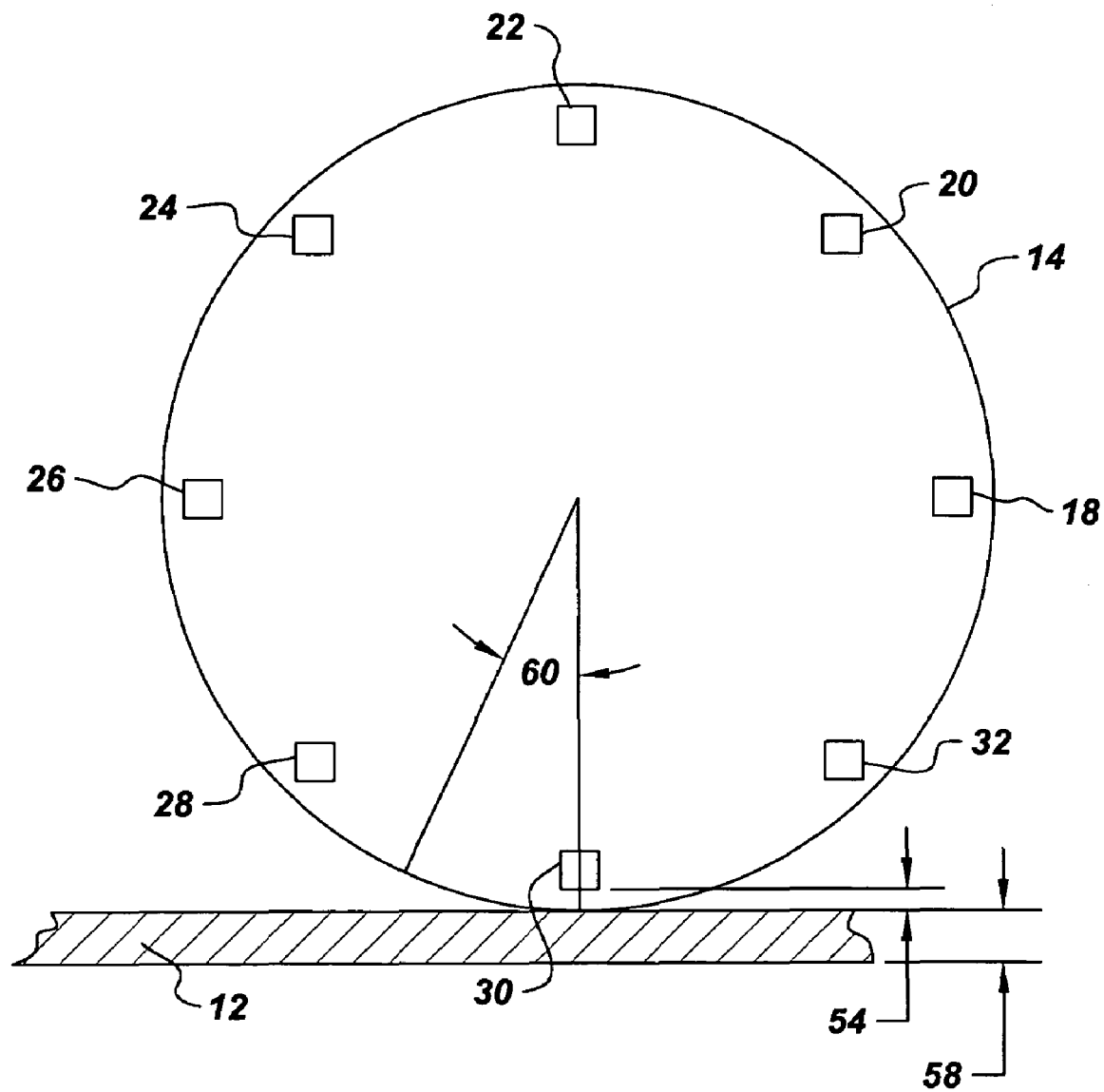
FIG. 3 is a front view of the rolling object illustrating various parameters of the object shown in FIGS. 1–2.

The relationship between the translation velocity of the rolling object and maximum speed '$V1_{max}$' of the sensor, when the sensor is active is described below. It may be noted that the horizontal component $v_x$ and $v_y$ that are representative of the horizontal (along track) and vertical (perpendicular to track) components of sensor velocity is described by the following equation:

$$v_x = V_c \left[1 - \frac{R-h}{R}\cos(\Delta\theta)\right] \quad \text{Equation (1)}$$

$$v_y = V_c \left[1 + \frac{R-h}{R}\sin(\Delta\theta)\right] \quad \text{Equation (2)}$$

where '$V_c$' is translation velocity of the rolling object, 'R' represents the radius of the rolling object, $\Delta\theta$ represents a span angle represented by reference numeral 52 in FIG. 3, and 'h' represents the height of the sensor from the surface of the three-dimensional volume, represented by reference numeral 54.

From equations 1 and 2, the speed of the rolling object can be represented by the following equation:

$$V_c \leq \frac{V1_{max}}{\left[1 - \frac{R-h}{R}\cos\left(\min\left(\frac{\pi}{s}, \Delta\theta_{min}\right)\right)\right]} \quad \text{Equation (3)}$$

The relationship between the translation velocity of the rolling object and 'time of flight' T of the sensor, which is equivalent to a scan-time or response time for the inspection system, when the sensor is active is described below.

$$V_c \leq \frac{R * \min\left(\frac{\pi}{s}, \Delta\theta_{min}\right)}{T} \quad \text{Equation (4)}$$

where $$T = \left(\frac{h}{v_l} + \frac{d}{v_s}\right) \quad \text{Equation (5)}$$

In Equations (4) and (5), 'd' represents the depth of the three-dimensional volume, 's' represents the number of sensors, '$v_s$' represents the speed of sound in the material used for implementing the three-dimensional volume, and '$v_l$' represents the speed of sound in the material used for implementing the rolling object. In one specific embodiment, d=0.20 meters, R=0.5 meters, $v_l$=2000 m/s and $v_l$=6000 m/s.

Each sensor in the inspection system is configured to receive signals indicative of a condition of the three-dimensional volume. For example, the sensor can be configured for detecting cracks on the surface of the three-dimensional volume. The sensors are also configured to detect deformities within the three-dimensional volume. Data received from ultrasound sensors contain strong reflection signals from cracks in the 3D volume. In one embodiment, a crack appears as a spike in graph plotting the signal strength to time. The presence and characteristics of these signals is used to detect and measure cracks.

Figure 4:
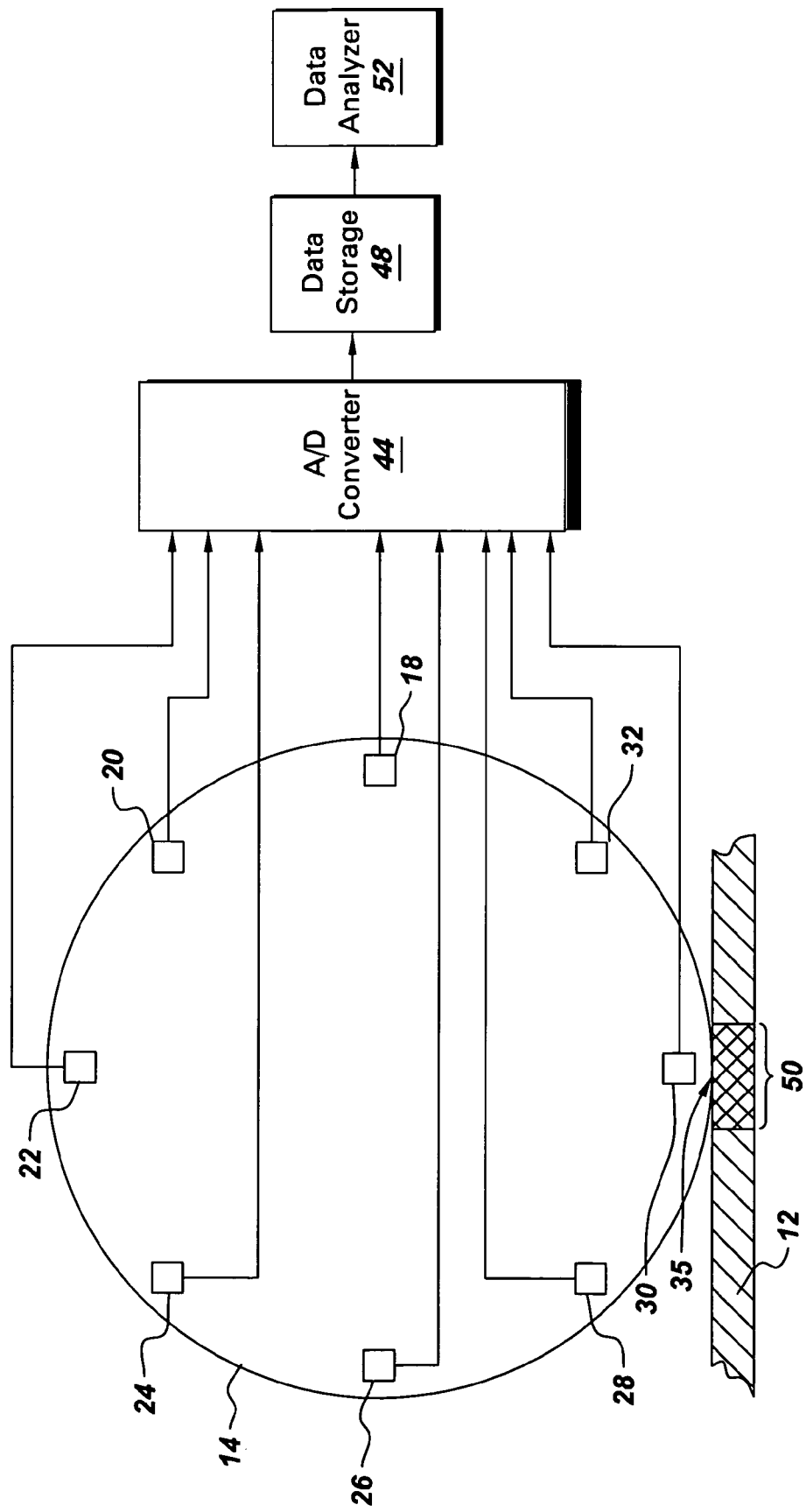
FIG. 4 is a block diagram illustrating an embodiment of an inspection system with a data analyzer.

FIG. 4 illustrates a more specific embodiment of an inspection system implemented according to one aspect of the invention. FIG. 4 illustrates the sensors being coupled to an analog to digital converter 44 a data storage device 48 which is in turn coupled to a data analyzer 52. Each component is described in further detail below.

The sensors are configured for sensing the integrity of three-dimensional volume 12. In one embodiment, the sensors are configured to generate analog signals corresponding to a condition of a region on the three-dimensional volume. For example, sensor 30 is configured to generate an analog signal representative of region 50. Similarly, each sensor generates signals representative of various regions of the three-dimensional volume 12.

Analog to digital (ADC) converter 44 coverts the analog signals received from the sensors to a corresponding digital signal. ADC 44 is coupled to data storage device 48. The data storage device is configured to store the digital signals for analysis. It may be noted that the data storage device 48 may be directly coupled to the sensors and configured to store the analog signals generated by the sensors.

Data analyzer 52 is configured for analyzing the digital signals representative of a condition in various regions of the three-dimensional volume. Examples of conditions include cracks on the surface of the three-dimensional volumes as well as cracks within the three-dimensional volumes. Data analyzer 52 may also be configured to determine other conditions such as deformities within the three-dimensional volume.

Figure 5:
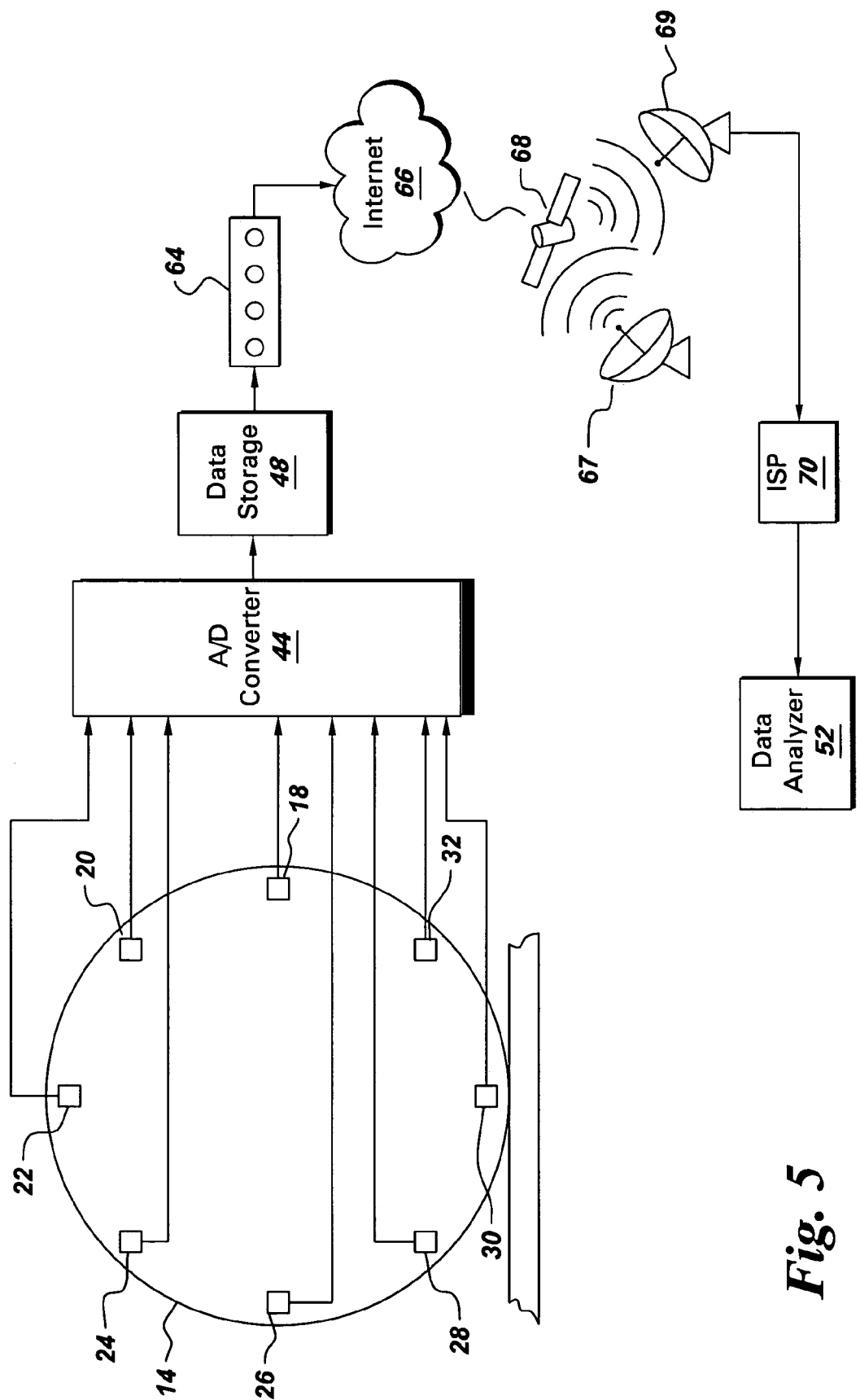
FIG. 5 is a block diagram illustrating an embodiment of an inspection system with a data analyzer located at a remote location.

In one embodiment as illustrated in FIG. 4, the data analyzer may be coupled to the rolling object 14. In another embodiment as illustrated in FIG. 5, the data analyzer may be located remotely and the data stored in the data storage device 48 is provided to the data analyzer for analysis. In an embodiment, the data analyzer comprises a data visualization system coupled to manual, semi-automatic or fully automatic defect or feature recognition module.

FIG. 5 illustrates an embodiment of the invention where the data analyzer 52 is in a remote location. FIG. 5 comprises rolling object 14, analog to digital converter 44 and data storage device 48. Modem 64 provides an ISP connection to a network such as internet 66. This invention is not limited to the use of the modem, and in particular, other network connection devices can be used like an integrated services digital network (ISDN), local-area-network (LAN), Ethernet, 10Base-T, 100Base-T, etc. that uses protocols such as an TCP/IP, AppleTalk, etc. Satellite 68 receives digital signals from the satellite dish 67. An ISP 70 receives the signals from the satellite 68 through another satellite dish 69 and sends them to data analyzer 52. Data analyzer analyzes the signals received to determine a condition of the three-dimensional volume.

Figure 6:
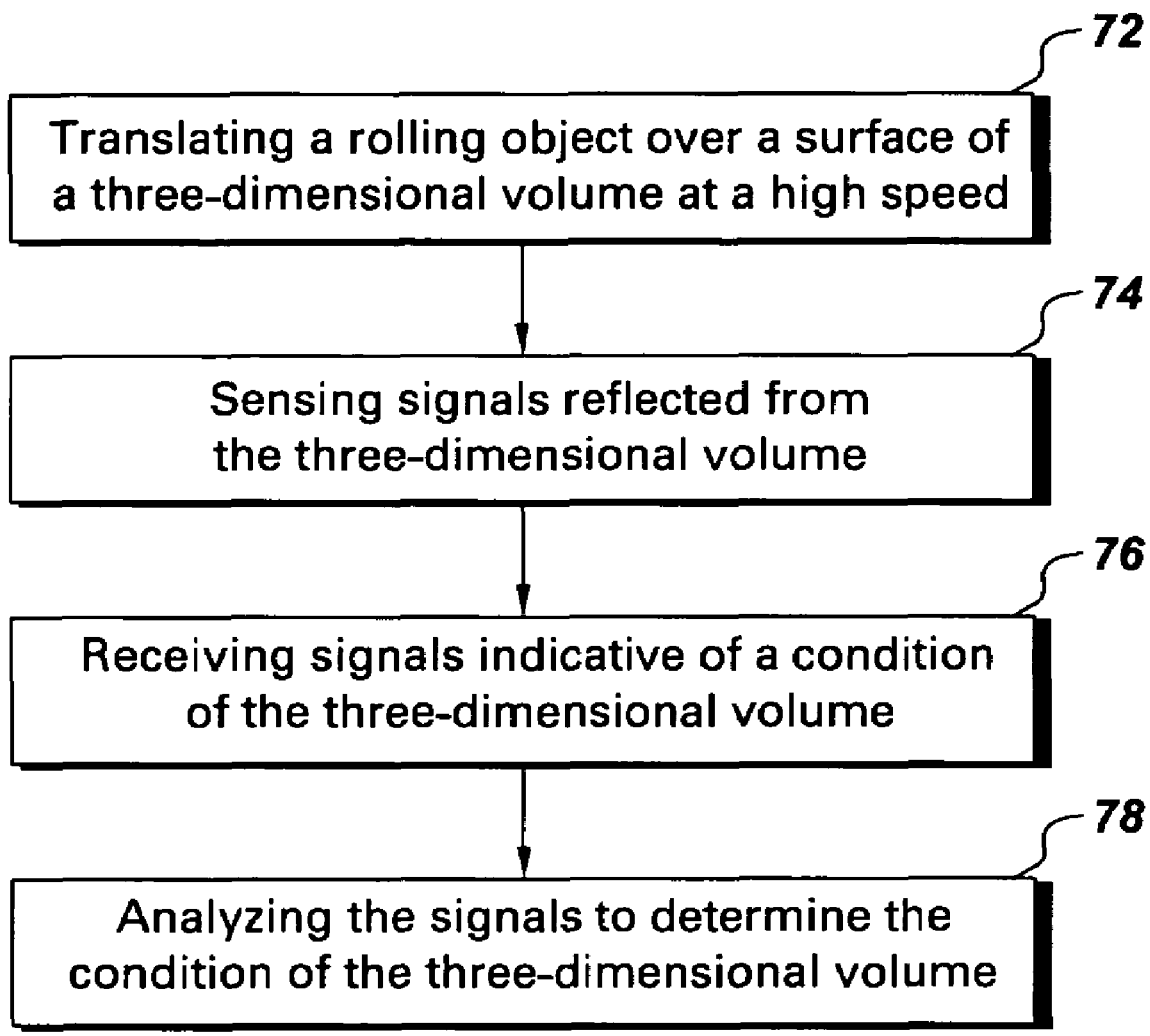
FIG. 6 is a flow chart illustrating one method by which an inspection system is implemented.

FIG. 6 is a flow chart illustrating one method by which a condition of a three-dimensional volume is determined. Each step in the flow chart is described in detail below.

In step 72, a rolling object is translated over a surface of the three-dimensional volume at a high speed. In one embodiment, the rolling object comprises at least one sensor coupled thereto, and is disposed on a non-contact outer region of the rolling object at a pre-determined distance from its center. In one specific embodiment, the rolling object is a wheel of a locomotive and the three-dimensional volume is a railway track.

In step 74, the signals reflected from the three-dimensional volume is sensed by the sensor. In an embodiment, the sensors comprise ultrasound sensors and the signals comprise ultrasound signals.

In step 76, the sensor receives the reflected signals. The reflected signals indicate a condition of the three-dimensional volume. In step 78, the reflected signals are analyzed to determine a condition of the three-dimensional volume. In one embodiment, the reflected signals are received from a data storage unit. In another embodiment, the reflected signals may be analyzed in real time. The analysis of the reflected signals result in determining the condition of the three-dimensional volume inspected and also provides information on a location of a particular defect.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. An inspection system for inspecting a three-dimensional volume, comprising;
    at least one sensor coupled to a rolling object, wherein the at least one sensor is disposed on a non-contact outer region of the rolling object and at a pre-determined distance from a center of the rolling object; wherein the at least one sensor is configured to generate signals representative of a condition of a region on the three dimensional volume; wherein the at least one sensor is an ultrasound sensor, and
    a data analyzer configured to analyze the signals to determine the condition of the three-dimensional volume at specific locations therein.

2. The inspection system of claim 1, wherein the at least one sensor is disposed at a periphery of the non-contact outer region of the rolling object.

3. The inspection system of claim 1, wherein the at least one sensor comprises a plurality of sensors disposed at a pre-determined distance from the center of the rolling object, and wherein a sensor closest to a point of rolling is active.

4. The inspection system of claim 1, wherein the at least one sensor is configured to receive signals indicative of a condition of the three-dimensional volume.

5. The inspection system of claim 1, wherein the rolling object is stationary.

6. The inspection system of claim 1, wherein the rolling object is in motion.

7. The inspection system of claim 5, wherein the data analyzer is at a remote location.

8. The inspection system of claim 1, wherein the rolling object comprises a wheel of a locomotive.

9. The inspection system of claim 1, wherein the three-dimensional volume is a railway track.

10. A method for inspecting a three-dimensional volume, comprising;
    translating a rolling object over a surface of the three-dimensional volume at a high speed, wherein the rolling object comprises at least one sensor coupled thereto, disposed on a non-contact outer region of the rolling object at a pre-determined distance from its center; wherein the at least one sensor is an ultrasound sensor, and
    sensing signals reflected from the three-dimensional volume as the rolling object translates over the three-dimensional volume.

11. The method of claim 10, wherein the sensing occurs from a periphery of a non-contact region of the rolling object.

12. The method of claim 10, further comprising receiving signals indicative of a condition of the three-dimensional volume.

13. The method of claim 12, further comprising, analyzing the signals to determine the condition of the three-dimensional volume at specific locations in the three-dimensional volume.

14. The method of claim 12, wherein the analyzing occurs in real-time.

15. An inspection system for inspecting a railway track, comprising;
    at least one sensor coupled to a wheel of a locomotive, wherein the at least one sensor is disposed on a non-contact outer region of the wheel and at a pre-determined distance from a center of the wheel; wherein the wheel is translating over the railway track at a high speed; wherein the at least one sensor is configured to generate a signal representative of a condition of a region on the railway track; wherein the at least one sensor is an ultrasound sensor, and
    a data analyzer configured to analyze the signals to determine the condition of the railway track at specific locations therein.

16. The inspection system of claim 15 wherein the at least one sensor is disposed at a periphery of the non-contact outer region of the wheel.

17. The inspection system of claim 15, wherein the at least one sensor comprises a plurality of sensors disposed at a pre-determined distance from the center of the wheel object, and wherein a sensor closest to a point of rolling is active.

18. The inspection system of claim 15, wherein the at least one sensor is configured to receive signals indicative of a condition of the railway track.

19. The inspection system of claim 15, wherein the data analyzer is coupled to the locomotive.

20. The inspection system of claim 15, wherein the data analyzer is at a remote location.

* * * * *